United States Patent [19]

Coleman et al.

[11] Patent Number: 5,456,885
[45] Date of Patent: Oct. 10, 1995

[54] FLUID COLLECTION, SEPARATION AND DISPENSING TUBE

[76] Inventors: Charles M. Coleman, 958 Washington Rd., Pittsburgh, Pa. 15228; William Kendrick, 34 Willowbrook Dr., Doylestown, Pa. 18901

[21] Appl. No.: 90,329

[22] Filed: Jul. 12, 1993

[51] Int. Cl.⁶ .................................................... B01L 11/00
[52] U.S. Cl. .............................. 422/101; 422/73; 422/99; 422/102; 436/177; 210/782; 210/789
[58] Field of Search ...................... 422/101, 100, 422/73, 102, 99; 436/177, 178; 210/782, 789, 787

[56] References Cited

U.S. PATENT DOCUMENTS

| | | | |
|---|---|---|---|
| 3,508,653 | 4/1970 | Coleman | 210/83 |
| 3,741,732 | 6/1973 | Stanfield | 73/425.4 |
| 4,104,025 | 8/1978 | Retzer | 23/230 |
| 4,308,232 | 12/1981 | Crouther et al. | 422/102 |
| 4,361,155 | 11/1982 | Anastasio | 128/763 |
| 4,579,828 | 4/1986 | Ali | 422/73 |
| 4,650,662 | 3/1987 | Goldfinger et al. | 422/102 |
| 4,853,137 | 8/1989 | Ersson | 422/101 |
| 4,877,520 | 10/1989 | Burns | 422/101 |
| 4,964,601 | 8/1990 | Fiehler | 422/101 |
| 5,053,134 | 10/1991 | Luderer et al. | 422/101 |
| 5,054,498 | 10/1991 | Melet | 128/763 |
| 5,059,398 | 10/1991 | Kenney | 422/100 |
| 5,065,768 | 11/1991 | Coleman et al. | 128/760 |
| 5,104,625 | 4/1992 | Kenney | 422/100 |
| 5,132,232 | 7/1992 | Parker | 436/177 |
| 5,203,825 | 4/1993 | Haynes et al. | 73/864.02 |
| 5,236,604 | 8/1993 | Fiehler | 422/101 |

*Primary Examiner*—Donald E. Czaja
*Assistant Examiner*—Lien Tran
*Attorney, Agent, or Firm*—Ingersoll Buchanan; Lynn J. Alstadt

[57] ABSTRACT

A tube for collection, separation and dispensation of a two-phase fluid is provided with a elongated rigid tubular container having a fluid entry end a closable end and a float. The float retained within the tubular container is positioned between the light phase and the heavy phase of the fluid on centrifugation thereby separating the two phases. In dispensing the light phase, the float moves to and engages the fluid entry end thereby preventing the heavy phase from escaping out of the tube.

24 Claims, 3 Drawing Sheets

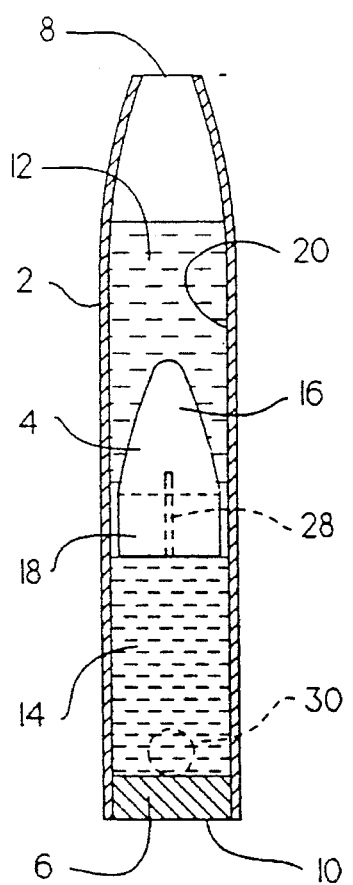
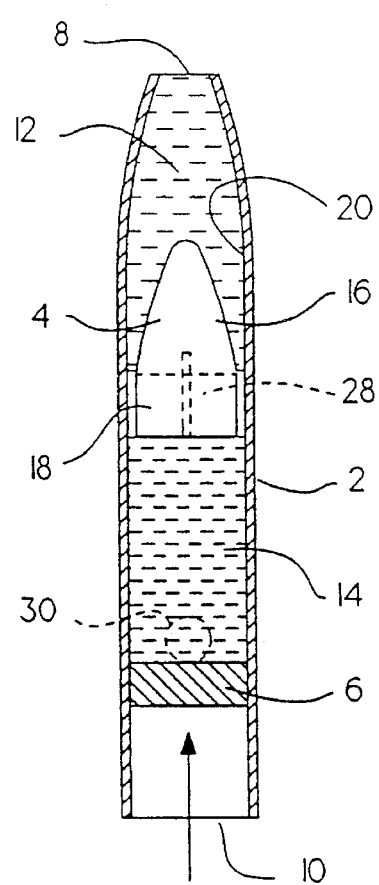
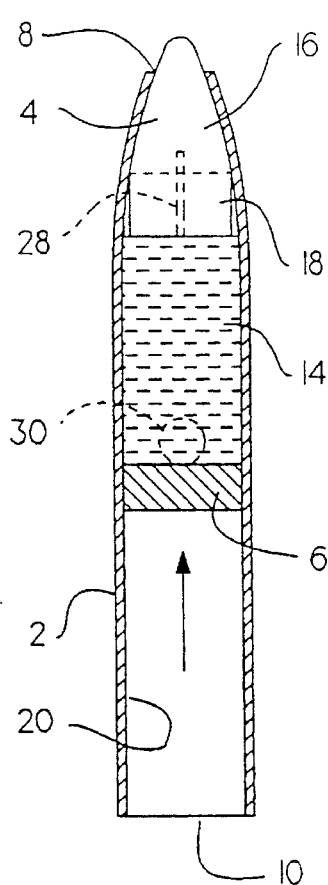
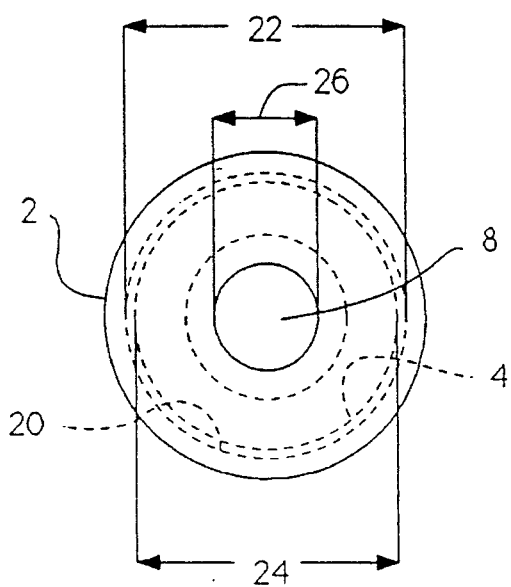
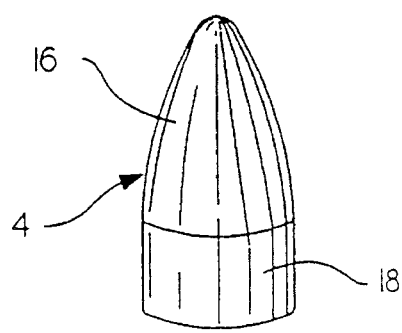

FLUID COLLECTION, SEPARATION AND DISPENSING TUBE

BACKGROUND OF THE INVENTION

1. Field of the Invention

The present invention relates to an apparatus which is used for collecting and separating a two-phase fluid and dispensing a light phase.

2. Description of the Prior Art

It is well known in the art to collect and centrifuge fluids, such as blood, in small bore or capillary tubes for clinical evaluation. It has been possible to collect blood specimens from skin punctures directly into narrow bore capillary tubes. The collection tube may then be placed in a centrifuge for separating the fluid into a light phase of serum or plasma and a heavy phase of blood cells. The separated serum is then analyzed. An anticoagulant may be added to the blood specimen before centrifugation if testing is to be performed on plasma.

Most tests are conducted on blood serum or blood plasma after it has been removed from the collection vessel. The tests may be performed on automated chemistry and immunological analyzers which require specified volumes of blood plasma for the diverse tests. These tests are generally used to determine the physical state and health of the individuals being tested. Hence, attainment of the highest precision and accuracy are essential requirements in blood analyses.

There are several means by which the plasma or serum is conventionally obtained from the collection tube. This is frequently accomplished by decanting, siphoning, or the use of a pipet or automated vacuum withdrawal cannula. One major problem encountered with respect to such testing is that as the serum or plasma is removed from the collection tube after centrifugation, it is often inadvertently mixed with the heavy phase thereby making the test result inaccurate. Thus, testing should be done for reliable results shortly after separation. If blood is centrifuged and the separated cells are left in contact with the liquid phase, glucose will move from the serum and be metabolized by the cells. The cation potassium leaks out of the cells with the passage of time and enters into the plasma. Other analyses may have been found to change with time. Consequently, the reliability of the analysis may diminish if timely analysis is not made on centrifuged blood.

Several means of obtaining and maintaining a better separation of blood fluid into a light phase and a heavy phase are known in the art. In the system illustrated in my U.S. Pat. No. 3,508,653, a resilient plunger is positioned within a tubular container closely adjacent a resilient stopper. The resilient plunger which is in sealing contact with the inner surface of the tubular container moves to the interface between the plasma and the cells on centrifugation, providing a permanent seal. However, in dispensing the light phase, in order to get a specific volume of sample it is necessary to use an additional device such as a pipet or a pipetter-dispenser to transfer the sample to the test vessel. If a gel is used as an equivalent separator element, use of a pipet or pipetter-dispenser is likely to cause greater contamination and inaccuracy than decantation from the collection tube directly to the test vessel.

In the system of my U.S. Pat. No. 5,065,768, a gel separator element may be placed within a capillary tube having a self-sealing plug at one end opposite a fluid entry end. The separator gel forms a seal between the light phase and the heavy phase of the blood on centrifugation. A plunger of a pipetter-dispenser pushes the self-sealing plug to dispense a measured quantity of the light phase sample. However, the gels employed have a tendency to adhere to the wall of the tube resisting movement and the cells usually thereby diffuse and contaminate the light phase sample.

In U.S. Pat. No. 5,203,825, Haynes et al. disclose a collection tube for examining the buffy coat layer. A plastic float is placed within a capillary tube having a vented cap at one end. On centrifugation, the float is positioned between the light phase and the heavy phase, after which the buffy coat layer is examined. However, this tube is not intended or designed to dispense the light phase. Indeed, the cap's flange base required to seal its vent obviates use of a pipetter-dispenser.

SUMMARY OF THE INVENTION

The present invention comprises a tube containing a float used in conjunction with a tube for collecting and separating a two-phase fluid and dispensing a light phase. The collection tube has a fluid entry end and a closable end. Preferably a self-sealing plug is used for the closable end. The tube preferably is a capillary tube which collects blood through capillary action into a tube having a self-sealing plug. Alternatively, a syringe plunger may be used to draw the blood into the tube. A piston head, i.e. a rubber tip which is disconnected from a syringe rod, is used for the closable end. After the blood is collected into the tube, which may or may not be completely filled, the blood can be immediately separated by centrifugation if an anticoagulant (such as heparin, EDTA or citrate) has been previously added to the collection tube in the proper amount.

The collection tube contains, in addition to the self-sealing plug, which permits collection, separation and dispensation of the separated light phase, a float element. The float has a specific gravity intermediate the specific gravity of the plasma or light phase and the blood cells or heavy phase. On centrifugation, the float is positioned between the light phase and the heavy phase, thereby preventing components in each phase from moving to the other phase. The float is sized and shaped so that there is a relatively narrow clearance between the walls of the float and the tube. Further, the fluid entry end of the tube is constricted so that the front of the float will engage and close that end when the float and accompanying cells reach end of the collection tube during the process of dispensing the light phase. In effect, this invention provides for an automatic check valve that halts flow at the end of the column of the separated plasma. This enables a separation and dispensation of blood and other bio-fluids with high purity and minimal operator technique.

In a tube with a self-sealing plug or a piston head at an end opposite the fluid entry end, the dispensation of specific volumes of the light phase sample is easily facilitated. The float moves easily, while floating in the packed cell/plasma interface with minimal resistance, to the fluid entry end by the pressure of a pipetter-dispenser rod or a syringe rod pushed against the plug or the piston head.

Other details, objects and advantages of the invention will become apparent as the following description of certain present preferred embodiments thereof proceeds. In the accompanying drawings I have shown certain present preferred embodiments of the invention.

A BRIEF DESCRIPTION OF THE DRAWING

FIG. 1 is a sectional view of a first preferred embodiment of my invention wherein the tube contains a blood sample which has been centrifuged. (The float is not shown in a sectional view.)

FIG. 2 is a sectional view of the embodiment of FIG. 1 after the self-sealing plug floating adjacent the packed cells has been pushed toward the fluid entry end and the light phase of the sample has been partially dispensed.

FIG. 3 is a sectional view of the embodiment of FIG. 1 after the float engages the fluid entry end.

FIG. 4 is an end view of the open fluid entry end of the embodiment of FIG. 1.

FIG. 5 is a perspective view of a preferred type of the float for use in the present invention.

DESCRIPTION OF THE PREFERRED EMBODIMENTS

Figure 6:
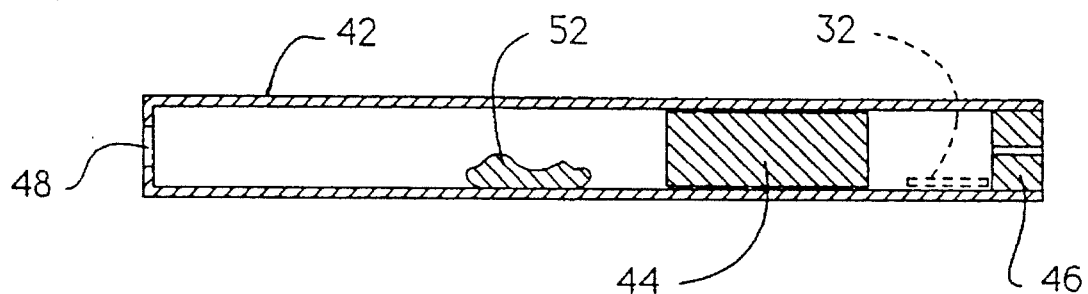
FIG. 6 is a sectional view of a second present preferred embodiment when the tube is empty.
Figure 7:
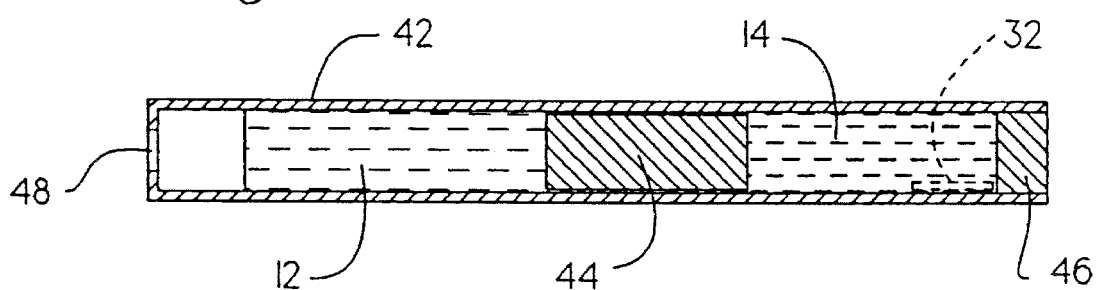
FIG. 7 is a sectional view of the embodiment of FIG. 6 containing a centrifuged blood sample.
Figure 8:
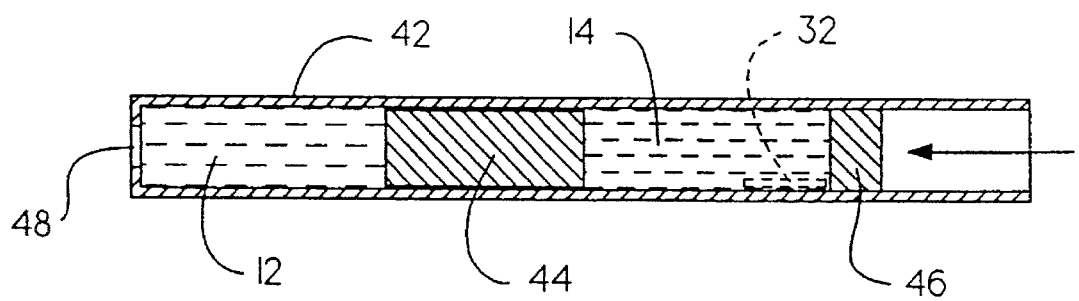
FIG. 8 is a sectional view of the embodiment of FIG. 7 after the self-sealing plug has been pushed toward the fluid entry end and the light phase of the sample has been partially dispensed.
Figure 9:
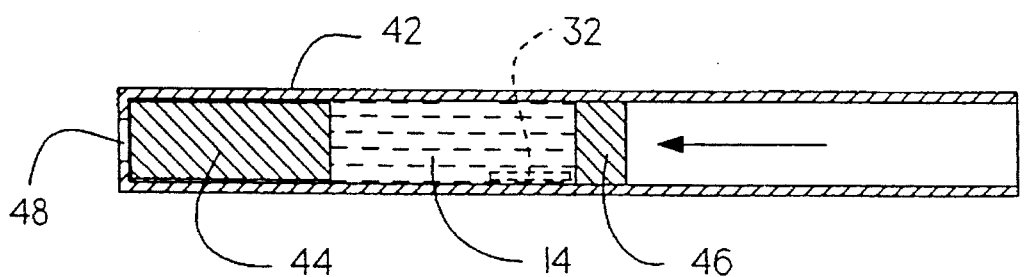
FIG. 9 is a sectional view of the embodiment of FIG. 7 after the light phase of the sample has been completely dispensed and the float blocks further dispensation.

A first preferred embodiment shown in FIGS. 1 through 5 is a tube for the collection, separation and dispensation of a fluid. The tube includes a tubular container 2 and a float 4. In its simplest form, the tubular container 2 is configured as a capillary tube. However, tubular containers of various sizes and shapes can be used.

The tubular container 2 is provided with a fluid entry end 8 and a closable end 10. The fluid to be collected, such as blood, enters the tubular container 2 through the fluid entry end 8. The closable end 10 is closed preferably by a self-sealing plug 6 of the type described and illustrated in my U.S. Pat. No. 5,065,768 which is incorporated herein by reference. After the fluid is separated into a light phase 12 and a heavy phase 14 as shown in FIG. 1, the light phase 12 is dispensed from the tubular container 2 through the fluid entry end 8. In the case of tubes with a self-sealing plug 6, the self-sealing plug 6 facilitates dispensation of a specific volume of the light phase 12 as the plug 6 moves by the pressure of a pipetter-dispenser.

The tubular container 2 contains a float 4. In order to retain the float 4, the opening diameter 26 of the fluid entry end 8 is less than the internal diameter 22 of the tubular container 2. The float diameter 24 is more than the opening diameter 26 and less than the internal diameter 22 of the tubular container 2 as shown in FIG. 4. We have found that a float having a diameter of 3.40 mm works well in a tube having an internal diameter of 3.57 mm and an opening diameter of 0.7 mm if the tubular container 2 is centrifuged at a relative centrifugal force of 11,000 G for five minutes in a microhematocrit centrifuge with a standard disc rotor modified to hold the tabular container 2.

The float 4 has a specific gravity intermediate the specific gravity of the light phase 12 and the heavy phase 14 enabling the float 4 to be positioned between the two phases after centrifugation as is shown in FIG. 1. The specific gravity of the float 4 ranges from about 1.035 to about 1.085, and preferably 1.036 to 1.046. In dispensing the light phase 12, the float 4 moves to and engages the fluid entry end 8 thereby blocking the heavy phase 14 from escaping out of the tubular container 2. Thus, the float 4 acts as an automatic check valve.

The float 4 is shaded so that there is relatively narrow clearance between the walls of the float 4 and the tubular container 2, sufficient to retain the cells from mixing with the dispensed plasma during dispensation. Wall clearance between the inner wall 20 of the tubular container 2 and the float 4 may vary from 0.02 mm, or even less, and upwards to 1.0 mm, or even more, as defined by the length of the float 4, and other factors. If the float 4 is fabricated from an elastic material and/or a compliant material, with the specific gravity required, the float 4 may even fit in contact with the innerwall 20. However, a soft float may deform and be forced through the partially constricted glass fluid entry end 8. In many cases, elastomeric conico-cylindrical floats of specific gravity of 1.04, for example, are practical for the blood collection tubes which are glass or plastic. A vulcanized elastomer or a thermoplastic elastomer such as polyether block amide resin blended with urethane, or polyolefin with a mineral filler is used to adjust the float to the required specific gravity described above.

Further, the leading front of the float 4 is shaped to have a top portion 16 of the float 4 which fits and conforms to the fluid entry end 8. A bottom portion 18 remains within the tubular container 2 as shown in FIG. 3. The float will first greatly reduce, and then halt the flow of the dispensed material as the float 4 and accompanying cells of the heavy phase 14 reach the fluid entry end 8. The float 4 is preferably of a conico-cylindrical ("channel buoy") type as is shown in FIG. 5. A conical type and a frusto-conical type may also be used.

The conico-cylindrical float 4 is used with collection tubes primarily with conical or similarly narrowed tips as shown in FIGS. 1 through 3. This type of tube also permits collection directly from skin punctures into tubes with no anticoagulant, so that serum produced subsequent to coagulation may be separated and dispensed. The pointed tip of the conico-cylindrical float 4 will thrust through a clot and allow good separation and retention of the cells when the G force is adequate. Floating balls, or even cylinders will not usually provide adequate force to become lodged at the serum-clot interface when the blood is coagulated, as in a plain tube or one containing a clotting accelerator of inorganic origin such as glass, silica, and kaolin, or thrombin, prothrombin, or other biologically derived clotting accelerators, such as certain snake venoms.

The float 4 may be fabricated by machining or molding. We prefer to use polymeric materials such as polystyrene, ABS (acrylamide-butadiene-styrene), and other materials having a specific gravity between blood cells and plasma. While the specific gravity may be between that of blood cells and serum, the preferred specific gravity for this purpose is about 1.04 to 1.05.

The float 4 may be constructed of two or more materials, but the final specific gravity should be as noted above. For example, a float 4 may be constructed from molded medium density specific gravity 0.94) polyethylene and a magnetic steel pin 28 specific gravity 7.8) in a ratio of about 8.2 to 1, which will provide a float whose specific gravity will be about 1.04. It can also have the capability of being moved back and forth with a ring magnet, especially a rare earth magnet, or an electromagnet, such as a solenoid, in a tube containing an anticoagulant. Such a float 4 with magnetic properties is useful in the event that it is desired to mix additives deposited in the tube.

These self-contained magnetic floats are not essential for magnetic mixing. A stirrer such as a steel ball 30 or wire segment 32 may be placed in the tubular container 2 and positioned between the float 4 and the self-sealing plug 6. We have found a 3/32" steel ball works well in a tube with an internal diameter of 3.57 mm described above. One might mix the anticoagulant itself if plasma is to be obtained, or clotting accelerators if serum is to be obtained.

Other reagents may also be added to the collection tubes for a reaction in the collection tube. Antibodies attached to relatively high density particles deposited in the tubular container 2 react with the blood, precipitating high density lipoproteins (HPL) and very low density lipoproteins (VLDL) during centrifugation into the heavy phase and retaining low density lipoproteins (LDL) in the light phase, permitting LDL cholesterol to be assayed directly. Dextran sulfate with magnesium chloride reacts directly with LDL and VLDL precipitating them into the high specific gravity cellular mass, leaving HDL cholesterol in the plasma to be analyzed. These reagents may also be added to collection tubes without a float.

Another suitable float 4 is composed of a top portion 16 and a bottom portion 18 as shown in FIG. 5. The top portion 16 is preferably of a conical shape and comprised of a material having a specific gravity which is not greater than that of the light phase. The bottom portion 18 is comprised of a material having a specific gravity which is greater than that of the light phase. Thus, the top portion 16 thrusts through the light phase, and the float 4 is positioned at the interface between the two phases. It will facilitate a further separation and dispensation of the light phase 12.

A second preferred embodiment shown in FIGS. 6 through 9 is a capillary tube 42 having a fluid entry end 48 and a self-sealing plug 46. The fluid entry end 48 of the capillary tube 42 is constricted. In the case of glass tubes flaming the tip slightly will provide sufficient constriction. The fluid entry end 48 is to be narrow enough to retain the float 44, but to permit facile flow on dispensation. A plain cylinder type float 44 can be readily used with glass or plastic capillary tubes 42 containing anticoagulants 52 such as heparin, EDTA, and citrate, or a conical tip may be combined with the cylinder. The cylindrical float 44 can be made by extrusion, and the conical tipped cylinders may be molded. Other functions of this second preferred embodiment are the same as those of the first preferred embodiment.

Figure 10:
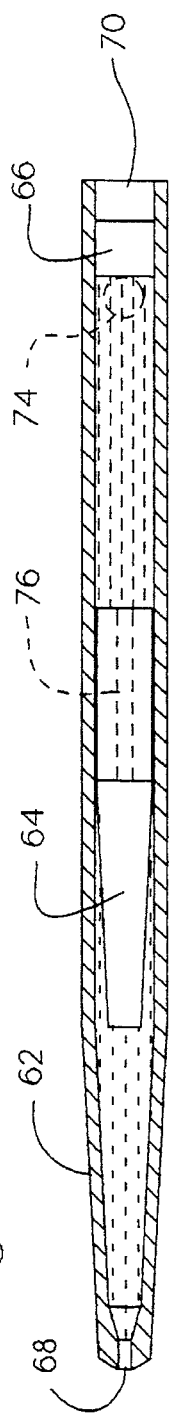
FIG. 10 is a sectional view of a third present preferred embodiment of my invention containing a blood sample which has been centrifuged. (The float and piston head are not shown in a sectional view.)
Figure 11:
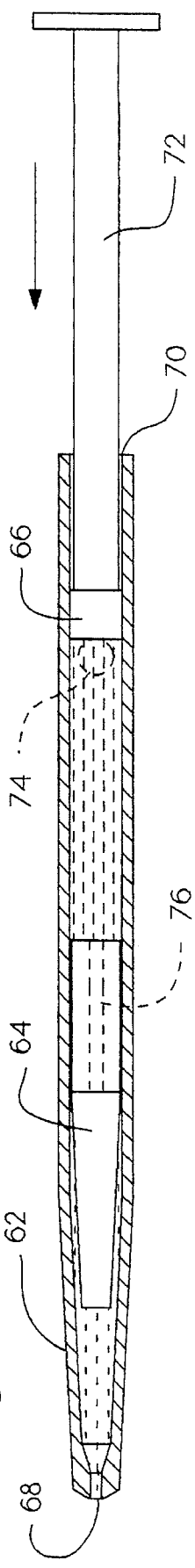
FIG. 11 is a sectional view of the embodiment of FIG. 10 after the piston head has been pushed toward the fluid entry end and the light phase of the sample has been partially dispensed. (The piston rod is not shown in a sectional view.)
Figure 12:
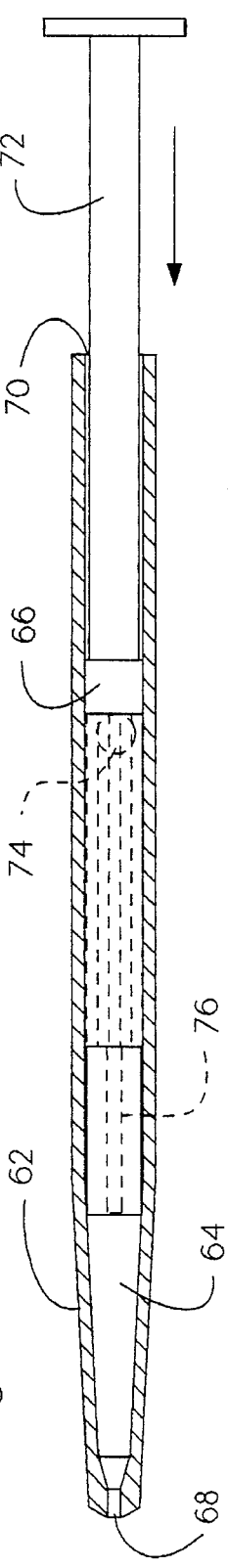
FIG. 12 is a sectional view of the embodiment of FIG. 10 after the light phase of the sample has been completely dispensed and the float blocks further dispensation.
Figure 13:
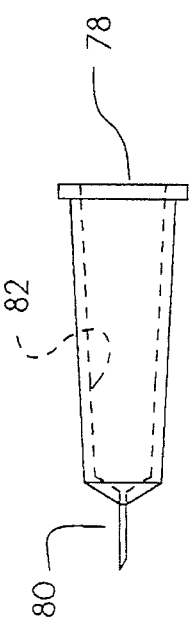
FIG. 13 is a perspective view of a preferred type of the needle for use in the embodiment of FIG. 10.

A third preferred embodiment of FIGS. 10 through 12 is a tubular container 62 having a fluid entry end 68 and a closable end 70. The closable end 70 is closed by a movable plug or piston head 66.

The fluid entry end 68 may be capped with a hypodermic needle assembly 78 which thereby converts this embodiment into a unique hypodermic syringe. This syringe permits withdrawal of an intravascular blood sample from a vein or artery when the piston head 66 is pulled back to the closable end 70 of the tubular container 62 by a piston rod 72 removably connected to the piston head 66. The hypodermic needle assembly 78 has a needle 80 such as an intravenous or intravascular needle and a cavity 82 into which the fluid entry end 68 fits. The needle 80 is preferably 1" to 1.5" in length. This embodiment may be utilized with a self-sealing plug rather than the syringe plunger. Venous or arterial blood will flow under vascular pressure to fill the tube automatically.

After the fluid is collected in the tubular container 62, the piston rod 72 is removed from the piston head 66, or the tube is placed directly into the rotor, and the fluid is centrifuged separating the fluid into two phases as shown is FIG. 10. As shown in FIG. 11, the piston rod 72 is attached to the piston head 66 again to push the piston head 66 thereby moving the float 64 toward the fluid entry end 68 of the tubular container 62, or the tube is placed into a dispenser if a self-sealing plug is used. Thus, the light phase 12 is dispensed from the fluid entry end 68 and the float 64 blocks the heavy phase 14 from escaping out of the tubular container 62.

The tubular container 62 may contain a stirrer such as a steel ball 74 or wire segment which moves back and forth several times with a ring magnet to mix the contents of the tubular container 62, which are to be centrifuged and handled as illustrated in the first preferred embodiment. Alternatively, a magnetic steel pin 76 can be inserted into a float 64, whose specific gravity will be about 1.04. Other functions of this third preferred embodiment are the same as those of the first preferred embodiment.

Although we have described and shown certain present preferred embodiments of my invention, it should be understood that the invention is not limited thereto but may be variously embodied within the scope of the following claims.

We claim:

1. A tube for collection and separation of a fluid having a lighter specific gravity phase and a heavier specific gravity phase in which tube the fluid can be separated and the lighter specific gravity phase can be dispensed therefrom comprising:

a. an elongated rigid tubular container which has a selected internal diameter, a fluid entry open end and a closable end, the fluid entry open end having an opening diameter which is less than the selected internal diameter;

b. a float positioned within the tubular container, the float having a float diameter which is less than the selected internal diameter of the tubular container and more than the opening diameter, the float having a specific gravity intermediate that of the lighter specific gravity phase and the heavier specific gravity phase enabling the float to be positioned between the two phases after centrifugation and act as a check valve in dispensing the lighter specific gravity phase by moving to and engaging the fluid entry open end thereby inhibiting the heavier specific gravity phase from escaping out of the tube; and c. closure means for closing the closable end to prevent the float and the fluid from flowing out of the tube, the closure means being sized and configured to be pushed through at least a portion of the tube toward the fluid entry open end by a force acting on the closure means to dispense the lighter specific gravity phase.

2. The tube of claim 1 wherein the elongated rigid tubular container is a capillary tube and the means for closing the closable open end is a self-sealing plug which permits air to pass therethrough.

3. The tube of claim 1 wherein the fluid is blood and the lighter specific gravity phase is plasma and the heavier specific gravity phase is blood cells.

4. The tube of claim 1 wherein the fluid is blood and the lighter specific gravity phase is serum and the heavier specific gravity phase is packed coagulum.

5. The tube of claim 1 wherein the float diameter is less than the selected internal diameter of the tubular container by about 0.02 mm to about 1.0 mm.

6. The tube of claim 1 wherein the float has a specific gravity of about 1.035 to 1.085.

7. The tube of claim 1 wherein the float is one of conical, frusto-conical, conico-cylindrical, and cylindrical.

8. The tube of claim 1 wherein the float is made of an polymeric material.

9. The tube of claim 8 wherein the float is made of one of a thermoplastic elastomer and a vulcanized elastomer.

10. The tube of claim 9 wherein the thermoplastic elastomer is selected from the group consisting of polyether block amide resin, urethane, polyolefin, and polystyrene.

11. The tube of claim 10 wherein the thermoplastic elastomer is mixed with a filler to get a specific gravity of about 1.04 to 1.05.

12. The tube of claim 1 wherein the float is formed of a material selected from the group consisting of polystyrene and acrylamide-butadiene-styrene.

13. The tube of claim 1 wherein the float is formed of at least two materials.

14. The tube of claim 13 wherein the float is formed of molded polyethylene and a magnetic steel pin in a ratio of 8.2 to 1 to attain a final specific gravity intermediate the specific gravity of the lighter specific gravity phase and the specific gravity of the heavier specific gravity phase.

15. The tube of claim 13 wherein the float has a top portion of a conical shape and a bottom portion, the top portion being comprised of a material having a specific gravity which is not greater than that of the lighter specific gravity phase, and the bottom portion being comprised of a material having a specific gravity which is greater than that of the lighter specific gravity phase.

16. The tube of claim 1 also comprising an anticoagulant within the tube which anticoagulant is selected from the group consisting of heparin, EDTA and citrate.

17. The tube of claim 1 also comprising a clotting accelerator within the tube which clotting accelerator is selected from the group consisting of silica, glass, kaolin, prothrombin, thrombin, and snake venoms.

18. The tube of claim 1 also comprising a stirrer within the tube which stirrer is one of a steel ball and a wire segment.

19. The tube of claim 3 also comprising antibodies within the tube which antibodies react with the blood and specifically precipitate high density and very low density lipoproteins into the heavier specific gravity phase and retain low density lipoproteins in the lighter specific gravity phase.

20. The tube of claim 3 also comprising reagents within the tube which reagents react with components within the blood.

21. The tube of claim 20 wherein the reagents are dextran sulfate and magnesium chloride which react with certain proteins in the blood.

22. The tube of claim 1 wherein the means for closing the closable end is a piston head and also comprising a piston rod removably connected to the piston head.

23. The tube of claim 22 also comprising a needle assembly which covers the fluid entry open end, the needle assembly having a hypodermic needle.

24. The tube of claim 23 wherein the needle is one of an intravenous needle and an intravascular needle and 0.75 to 2.0 inches long.

* * * * *

UNITED STATES PATENT AND TRADEMARK OFFICE
CERTIFICATE OF CORRECTION

PATENT NO. : 5,456,885
DATED : October 10, 1995
INVENTOR(S) : CHARLES M. COLEMAN, WILLIAM KENDRICK It is certified that error appears in the above-indentified patent and that said Letters Patent is hereby corrected as shown below:

Column 5, line 9, before "specific" add a parenthesis.

Column 5, line 10, before "specific" add a parenthesis.

Column 6, line 18, change "is" to --in--.

Column 7, line 20, claim 8, change "an" to --a--.

Signed and Sealed this

Twenty-seventh Day of February, 1996

Attest:

BRUCE LEHMAN

Attesting Officer

Commissioner of Patents and Trademarks